US011332296B2

(12) United States Patent
Roesler et al.

(10) Patent No.: US 11,332,296 B2
(45) Date of Patent: May 17, 2022

(54) MEMBRANE PACKAGING FOR STERILE, MEDICAL OBJECTS

(71) Applicants: Peter Roesler, Wangen (DE); Thiemo Roesler, Wangen (DE)

(72) Inventors: Peter Roesler, Wangen (DE); Thiemo Roesler, Wangen (DE)

(73) Assignee: ROESLER IP GMBH

( * ) Notice: Subject to any disclaimer, the term of this patent is extended or adjusted under 35 U.S.C. 154(b) by 47 days.

(21) Appl. No.: 16/677,038

(22) Filed: Nov. 7, 2019

(65) Prior Publication Data

US 2020/0172314 A1 Jun. 4, 2020

(30) Foreign Application Priority Data

Dec. 3, 2018 (DE) .............................. 102018130686

(51) Int. Cl.
*B65D 81/07* (2006.01)
*A61B 17/86* (2006.01)

(52) U.S. Cl.
CPC ............ *B65D 81/07* (2013.01); *A61B 17/865* (2013.01)

(58) Field of Classification Search
CPC ........ B65D 81/07; B65D 81/02; B65D 81/00; B65D 81/133; B65D 81/05; B65D 81/075; A61B 17/865
USPC ....... 206/438, 477, 478, 493, 591, 583, 265, 206/564, 1.5, 210, 223, 730, 7, 32, 735, 206/363, 63.5, 480, 488
See application file for complete search history.

(56) References Cited

U.S. PATENT DOCUMENTS

| 2,681,142 | A |   | 6/1954  | Cohen          |              |
|-----------|---|---|---------|----------------|--------------|
| 3,487,921 | A |   | 1/1970  | Barth et al.   |              |
| 3,669,337 | A |   | 6/1972  | Struble        |              |
| 4,491,225 | A | * | 1/1985  | Baillod ............... | B65D 81/075  |
|           |   |   |         |                | 206/583      |
| 4,903,827 | A |   | 2/1990  | Phelps et al.  |              |
| 5,251,760 | A | * | 10/1993 | Smith .................. | B65D 5/5028  |
|           |   |   |         |                | 206/583      |
| 5,348,549 | A | * | 9/1994  | Brown .................. | A61B 50/36   |
|           |   |   |         |                | 206/366      |
| 5,405,000 | A | * | 4/1995  | Hagedon ............. | B65D 81/075  |
|           |   |   |         |                | 206/216      |
| 5,769,235 | A |   | 6/1998  | Keach et al.   |              |
| 5,893,463 | A |   | 4/1999  | Krofchak et al. |             |
| 5,988,387 | A |   | 11/1999 | Staal et al.   |              |

(Continued)

FOREIGN PATENT DOCUMENTS

CH 630313 A5 6/1982
DE 3440169 A1 5/1986
(Continued)

*Primary Examiner* — Rafael A Ortiz
(74) *Attorney, Agent, or Firm* — Dentons Cohen & Grigsby P.C.

(57) ABSTRACT

Container with a membrane packaging for medical objects, consisting of at least one cover which is connectable to a lower part, wherein at least one clamping membrane is circumferentially and peripherally attached to at least one container part, and the object to be protected lies upon the at least one clamping membrane and is borne by it, wherein only one clamping membrane, is given, which lies opposite to a fixed holding slot for holding the object on the other container part and an additional pretensioning can be applied to the clamping membrane upon closing of the container.

16 Claims, 7 Drawing Sheets

(56) References Cited

U.S. PATENT DOCUMENTS

| | | | | |
|---|---|---|---|---|
| 6,880,706 | B2* | 4/2005 | Braconnot | B65D 81/07 |
| | | | | 206/363 |
| 6,889,839 | B1* | 5/2005 | Rosten | B65D 81/075 |
| | | | | 206/363 |
| 7,114,617 | B2* | 10/2006 | Yewdall | A61F 15/001 |
| | | | | 206/440 |
| 9,504,544 | B2* | 11/2016 | Conley | A61C 7/14 |
| 2005/0011807 | A1 | 1/2005 | Dennison et al. | |
| 2010/0140124 | A1* | 6/2010 | Hafner | A61F 2/0095 |
| | | | | 206/363 |
| 2013/0075282 | A1* | 3/2013 | Cinader, Jr. | B65B 5/04 |
| | | | | 206/63.5 |
| 2014/0299498 | A1* | 10/2014 | Neal | A61J 1/00 |
| | | | | 206/438 |
| 2014/0374282 | A1* | 12/2014 | Cinader, Jr. | A61C 19/02 |
| | | | | 206/63.5 |

FOREIGN PATENT DOCUMENTS

| | | |
|---|---|---|
| DE | 69300566 T2 | 5/1996 |
| JP | 200475072 A | 3/2004 |
| JP | 2004182313 A | 7/2004 |
| JP | 2005153952 A | 6/2005 |
| JP | 201291311 A | 5/2012 |

\* cited by examiner

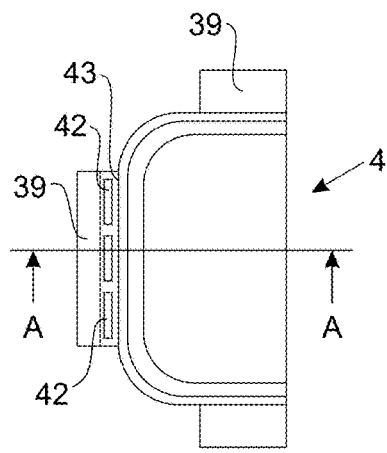
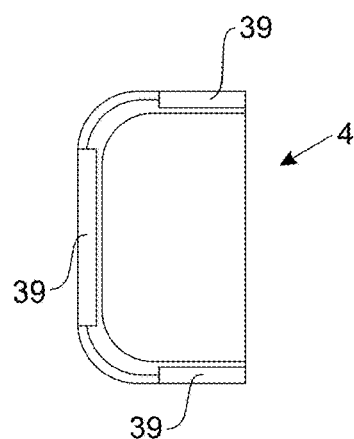
Fig. 24  Fig. 25
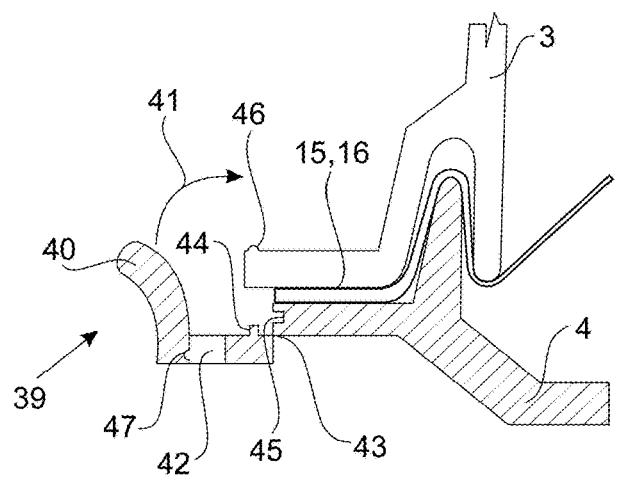
Fig. 26
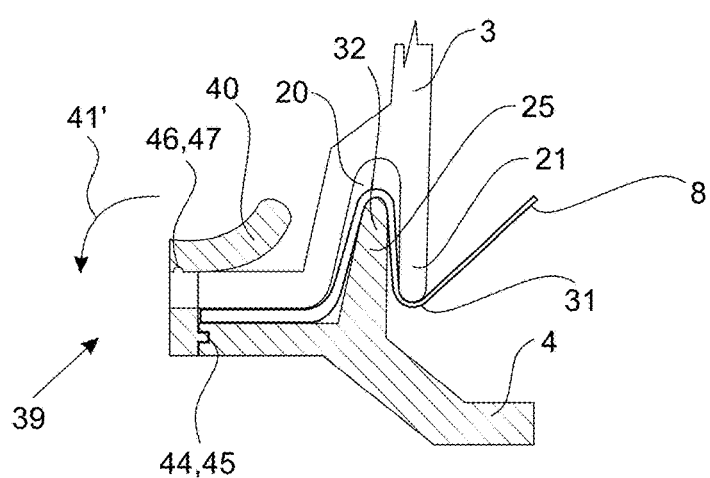
Fig. 27

MEMBRANE PACKAGING FOR STERILE, MEDICAL OBJECTS

FIELD OF THE INVENTION

The object of the invention is a membrane packaging for sterile medical objects.

BACKGROUND OF THE INVENTION

Unsterile membrane packaging has become known in a variety of embodiments. For example, reference is made to CH 630 313 A5, wherein two membranes opposite each other are present, between which the object to be protected is accepted.

For the pretensioning of the two membranes, two membrane clamping rings with negligibly deviating diameters are used, which, coaxially inserted into each other, pretension the two membranes against one another.

Such a membrane packaging is used primarily for packaging clock parts, such as small-part screws, crowns, hands, housing and more.

The disadvantage of such packaging is, however, that only relatively lightweight objects can be packaged, regardless of the tightness of the packaging surrounding the membrane. It would therefore not be possible to provide a packaging for the sterile protection of medical objects with such a packaging. In particular, no sterile implants could be stored in such a known packaging, because the peripheral sealing of the membranes in the surrounding packaging is not relevant.

The same criticism also applies to the object of U.S. Pat. No. 2,681,142, where a relatively lightweight object to be held is clamped between two pretensioned membranes, and the packaging container consists of a top part and a lower part, wherein the two parts are connected to each other with the help of a clamping edge.

Here, no value is placed on the tightness of the surrounding packaging in which the two membranes are clamped.

In U.S. Pat. No. 4,903,827 A1, two membranes are used, between which the object to be held is accepted, wherein, in order to improve the holding, the object is fixed in a container part against slots that open upwards, whereby an improved pretensioning and holding is possible even for heavy objects.

U.S. Pat. No. 3,487,921 describes a packaging for the holding of heavy objects, however no precautions are taken to additionally support the heavy object to be held in the interior of the surrounding packaging.

DE 34 40 169 A1 describes a folding packaging, wherein membranes opposite one another in both the cover as well as the lower part are provided, between which the object to be held can be clamped.

DE 603 13 690 T2 discloses a container for the floating packaging of a product. According to FIG. 1, the container forms a supporting frame for an internal shell, which in turn has placement zones for an autonomous sub-unit with a supporting frame. A foil is clamped over the supporting frame, on which the product to be packaged is placed. The supporting frame is then closed with a cover.

According to FIG. 1, the cover can have a filling or, according to FIG. 5, an element that exerts a pressure force on the product to be packaged when the cover is closed, so that the foil is pushed into the interior of the shell. Both the filling as well as the element have only one smooth surface, which is in contact with the product to be packaged. As a result, no adequate fixation of the product can be achieved.

In addition, the product must be pressed relatively far into the foil in order to achieve adequate fixation of the product.

In JP 2004-75 072 A, the object to be packaged is arranged between two foils. However, no heavy objects can be held due to the elasticity of the two foils.

SUMMARY OF THE INVENTION

The invention is therefore based upon the task of further developing a packaging of the type specified above such that a position-safe holding of sterile items is achieved within the packaging.

In order to achieve this task, the invention relates to a container with a membrane packaging for medical objects. The container comprises at least one cover which is connectable to a lower part, wherein a clamping membrane is circumferentially and peripherally attached to at least one container part, and an additional pretensioning is applicable to the clamping membrane upon closing of the container, in that the object to be protected pushes the clamping membrane into the interior of the container part. Further, a fixed fixing device for holding the object is arranged on a container part, wherein the clamping membrane of the fixed fixing device is opposite the other container part.

Thus, the invention differs from the prior art through the preferred feature that only a single clamping membrane is present, which lies opposite to a fixed holding slot for holding the object on the other container part, and an additional pretensioning can be applied to the clamping membrane upon closing of the container.

A preferred feature of the invention is therefore that only a single membrane is present, which is present in a peripherally sealed manner either in the cover or in the lower part, so that the object to be held is initially held on a—lying opposite to a membrane—solid holding surface on the one foldable container part, while the membrane is arranged on the other container part.

Another preferred feature provides that the membrane is now designed as a clamping membrane, and a pretensioning peripheral to the container is applied to the clamping membrane upon closing of the surrounding packaging.

The container part, which accepts the clamping membrane in a circumferentially sealed manner, thus forms a clamping edge, which, through the interlocking of the two container parts upon closing of the container parts, leads to a circumferential, peripheral pretensioning of the clamping membrane on all sides.

For the sake of simplifying the description, it is assumed in the following description that the clamping membrane according to the invention is arranged on the cover and that the fixed holding surface for holding the object to be held is arranged on the lower part.

However, the invention is not limited to this. It remains completely open which part of a two-part container is designated as a lower part or as a cover. The two terms are therefore interchangeable. Purely for the sake of simplifying the description, it is assumed in the following description that the clamping membrane is arranged in the cover at the cover's open upper side running all the way around it, and the fixed holding surface for the object to be protected is arranged on the lower part.

All embodiments of the invention have in common that either [sic] the container is pivotable as at least a two-part container in a horizontal pivotal axis and thus the cover is fastened on the lower part in a horizontal pivotal axis. However, the invention is not limited to this.

In another embodiment, it can be provided that the two container parts can be completely separated from one another. In this case, it is preferred that the cover can be circumferentially latched or plugged onto the lower part. For this purpose, special latch or plug connections will be described later. With this plug-in or plug-latch connection, the sealing of the container is enabled, and, at the same time, the clamping membrane is held under pretensioning.

Accordingly, it is advantageous that for the first time medical objects can be held in that the clamping membrane—preferably arranged in the cover—is now additionally pretensioned by attaching or unfolding the cover, and with the additional pretensioning, simultaneously circumferential sealing surfaces can be created on the container edge side, which ensure an absolute sealing of the object arranged in the container against the atmosphere.

It is preferred that an additional holding effect is achieved for the object to be held by means of an additional deformation of the clamping membrane in that the clamping membrane covers an interior of the cover that is sealed against the atmosphere.

If the lower part with the object to be held is pivoted or plugged onto the clamping membrane (lowered), the object that is located on one side of the clamping membrane pushes the clamping membrane like a piston into in the air-filled interior of the cover, resulting in a compression of the air contained therein, said compression air now additionally ensuring a further pretensioning and deformation of the clamping membrane. Thus, the clamping membrane not only attaches to the external perimeter of the object to be protected due to its mechanical clamping force, but it also forms a bulge-like, convex deformation due to the counter-pressure of the compression air, which forms an additional attaching area on the external perimeter of the object to be held and additionally fixes the object.

Later, it will be also described that—in the case of transparent packaging parts—the bulge-like deformation that is visible from the outside is a readily visually inspectable indicator for the tightness of a sterile packaging.

Another significant effect due to the pretensioning of the clamping membrane is that, due to the tensile movement on the clamping membrane, the peripheral surfaces of the clamping membrane are now also pretensioned, and, according to the invention, it is provided that in these peripherally circumferential areas where the clamping membrane is connected to the cover, one or more effective sealing surfaces are arranged.

It is advantageous when, due to the increase of the pretensioning of the clamping membrane by pivoting or slipping the cover, the sealing effect in the peripheral areas of the cover is now increased by arrangement of a container-side clamping edge. For this purpose, it is provided that the clamping membrane is circumferentially permanently fixed on the container edge at a weld seam, and a clamping groove extends radially inwards from the weld seam, which is freely covered by the membrane, and a ring clamping edge of the opposite lower part can be driven into this clamping groove, whereby the membrane is additionally pretensioned. A special form of a container-side clamping edge is thus described.

A first sealing surface is thereby created between a ring clamping edge of the lower part and the assigned opposite clamping groove in the area of the cover, wherein the ring clamping edge forms a first sealing finger, seen in profile.

Preferably, a second sealing surface is also formed, such that the clamping groove, which is arranged in the cover, has a circumferential second ring clamping edge running radially inwards, which also comes into contact with the membrane and additionally pretensions the membrane. This second ring clamping edge also forms a sealing finger seen in profile.

There is thus a double pretensioning by two ring clamping edges (sealing fingers) which point in opposite directions and interlock with one another, of which one is arranged in the cover and the other is arranged in the lower part.

As a result, two radially spaced sealing points are created, which ensure an absolute tightness of the hermetically sealed container.

Thus, it is possible for the first time to store sterile objects in such a container, because, by introducing the object into the container, the ring clamping edges that interlock with one another and run past one another with negligible clearance, also called sealing fingers, for the first time ensure a double sealing in the interior of the container due to the membrane and thus form two circumferential sealing edges that are radially distanced from one another.

Thus, it is possible for the first time to store sterile objects in such a container for a long period of time, because, due to the tensioning, the tensioning effect of the clamping membrane is increased upon interlocking or swiveling from the cover to the lower part, and thus the sealing effect in the area of the two radially spaced sealing edges is simultaneously increased.

In a preferred embodiment, it is provided that the clamping membrane according to the invention consists of a high-elastomer material, such as a sealable or weldable plastic material. It is preferably a polymer plastic which is highly elastic.

In a preferred embodiment, it is provided that, due to the presence of a single membrane, appropriate fixed fixing devices are arranged on the one container part, which are also able to hold relatively heavy objects. Such a fixing device can be, for example, a plug-in device, a clamping device, a screw-on device, or the like. The type and formation of the fixing device depends on the type and formation of the object to be held.

For example, if the object to be held has a screw thread, it can be screwed, slipped, or clamped onto an assigned holding surface on the one container.

Likewise, it is possible to use fixed clamping slots or the like on a container part.

It is advantageous for the invention that, due to the presence of a single membrane—omitting an opposite membrane—now relatively heavy objects can be held on a fixed holding surface on the one container part, and the single membrane only serves to fix the object and simultaneously provide an improved clamping sealing effect upon closing of the packaging, whereby on the one hand the holding force on the object to be held is increased and, on the other hand, the sealing effect is increased in the sealing edges of the container parts opposite one another.

The object of the present invention results not only from the object of the individual claims, but also from the combination of individual claims.

All information and features disclosed in the documents, including the abstract, in particular the spatial configuration shown in the drawings, could be claimed as essential to the invention, insofar as they are individually or in combination novel with respect to the state of the art. The use of the terms "essential" or "according to the invention" or "essential to the invention" is subjective and does not imply that the thusly labeled features must necessarily be a component of one or more claims.

BRIEF DESCRIPTION OF THE DRAWINGS

The invention is explained in more detail in the following on the basis of drawings, showing only one possible design. Further essential features and advantages of the invention will emerge from the drawings and their description.

The figures show:

FIG. 24 shows the top view on another embodiment of a lower part with clamping locks in the open state.

FIG. 25 shows the same illustration as FIG. 24 with the clamping locks in the closed state.

FIG. 26 shows a cross-section through the latch connection between the cover and the lower part in the open state.

FIG. 27 shows the same cross-section as FIG. 26 in the closed state.

DETAILED DESCRIPTION OF THE INVENTION

Figure 1:
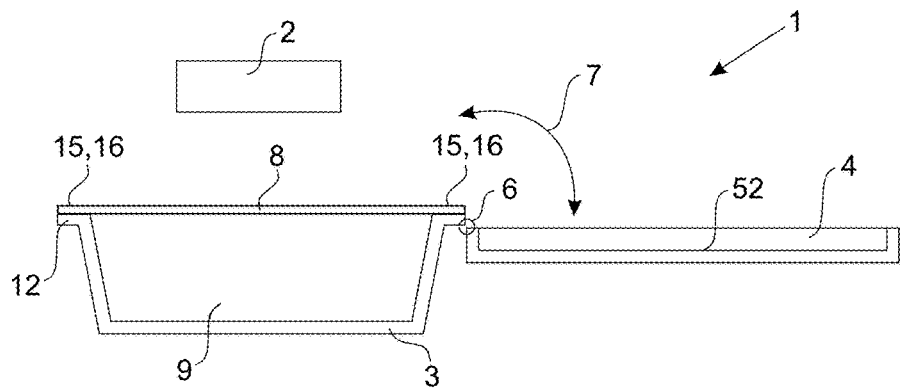
FIG. 1 shows a first embodiment of a container with a pivotable cover that is pivotable onto a lower part.
Figure 2:
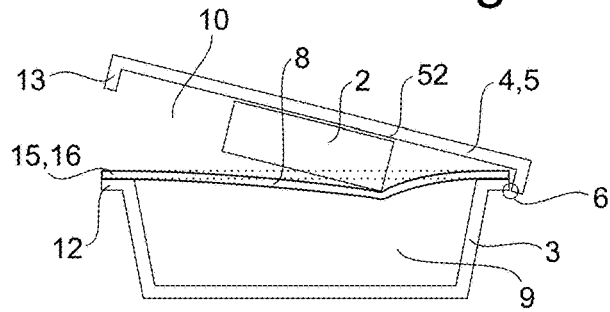
FIG. 2 shows the same illustration as FIG. 1 with an object to be held shortly before the closure position.
Figure 3:
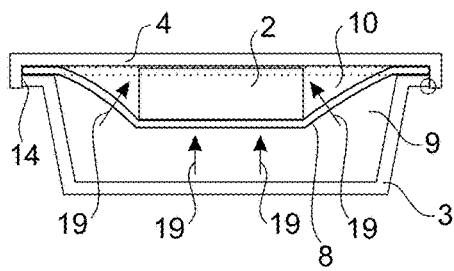
FIG. 3 shows the completed closure position of the container according to FIGS. 1 and 2.

In the exemplary embodiment according to FIGS. 1 to 3, the container 1 is designed as a pivoting container, for which a lower part 4 is pivotable onto a cover 3, which is covered by a clamping membrane 8, by means of a horizontal pivotal axis 6 in the direction of the arrow 7.

The object 2 to be held is accepted on a holding surface 52 on the inside of the lower part 4 and fixed there.

Upon pivoting the cover 3 opposite to the direction of the arrow 7, the object 2 to be held is thus clamped between the holding surface 52 on the inside of the lower part 4 and the clamping membrane 8, which covers the interior 9 of the cover 3 in a fully sealed fashion.

Here, it is provided that the clamping membrane 8 is sealed on a circumferential sealing edge 15 and a sealing surface 16 arranged there.

Such a sealing surface 16 can be provided, for example, by an ultrasound welding, through a laser welding, or through other measures or other welding methods, i.e. the clamping membrane 8 can be sealed all the way around on the assigned edge 12 of the cover 3 and sealed or welded on in a high-load fashion.

FIG. 2 now shows that when pivoting the cover 3 onto the lower part 4, the clamping membrane is tensioned and, because now the object 2 simultaneously pushes the clamping membrane 8 into the interior 9 of the cover 3, a compressed air over-pressure arises there, which affects the clamping membrane in the direction of the arrow 19 and additionally deforms the clamping membrane in a bow-like manner, such that it—due to the bow shape—attaches even further to the perimeter of the object 2 to be held. Thus, upon pivoting of the cover 3 onto the lower part 4, the holding effect on the object 2 is not only improved through the elasticity of the clamping membrane 8, but also in that the air present in the interior 9 is compressed and leads to an additional bulge-like deformation of the clamping membrane 8 in the direction of the arrow 19.

Figure 4:
FIG. 4 shows a schematic view of the illustration of a clamping membrane in cross-section.
Figure 5:
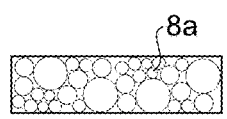
FIG. 5 shows the clamping membrane 8a in the untensioned state in cross-section, enlarged.
Figure 7:
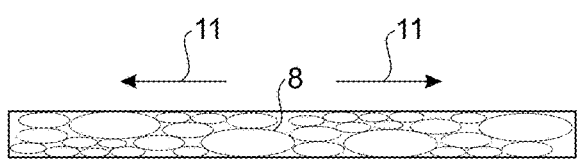
FIG. 7 shows the expansion of the clamping membrane 8a according to FIG. 5 when applying a tensile force.

In FIGS. 4 to 7, various types of clamping membranes 8 are shown, wherein a clamping membrane 8a is shown in FIG. 5, which shows air-filled intermediate spaces and has a round molecular structure, which is elastically deformed when a pretensioning is applied in the direction of the arrow 11.

Figure 6:
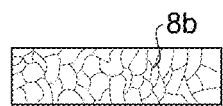
FIG. 6 shows an embodiment of a clamping membrane 8b modified from FIG. 5 with a different polymer structure in an enlarged cross-section.

FIG. 6 shows a different structure of a clamping membrane 8b, which has a linked molecular structure.

Figure 8:
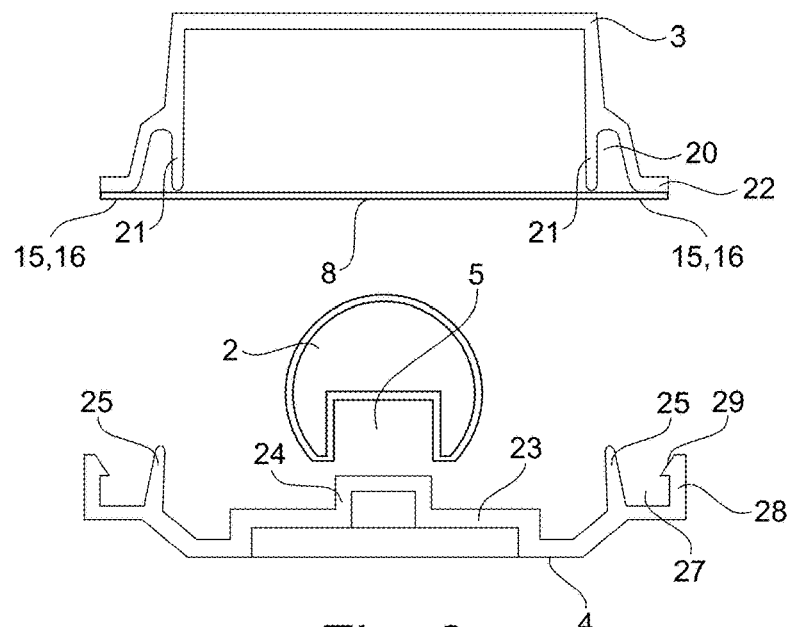
FIG. 8 shows a second embodiment of a container in a separated state in which an object is taken out of a clamp holding.
Figure 9:
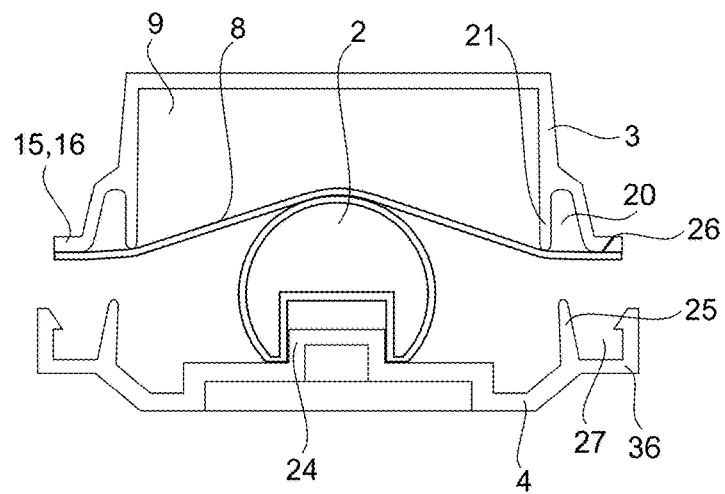
FIG. 9 shows the same illustration as FIG. 8 shortly before sealing of the container.
Figure 10:
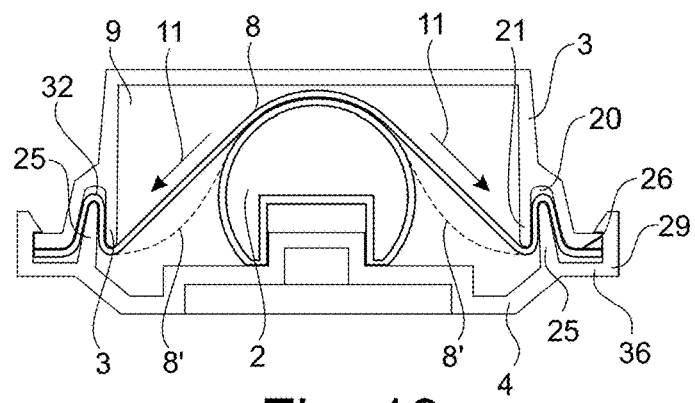
FIG. 10 shows the completely sealed container according to FIGS. 8 and 9.

In addition to the improvement of the holding effect of the object 2 by pivoting the lower part 4 into the cover 3, there is another advantage, which is illustrated in FIGS. 8 to 10 in schematic view. There, it is shown that, due to the pivoting and pretensioning of the clamping membrane 8 in the direction of the arrows 11, the sealing effect between the cover 3 and the lower part 4 is additionally increased in that the clamping membrane 8 is additionally clamped in the area of two sealing fingers 21, 25 facing each other and thus receives an additional pretensioning in the direction of the arrows 11.

In a preferred embodiment according to FIGS. 8 to 10, this is achieved in that a circumferential sealing finger 21 is present on the inner perimeter of the cover 3, which forms a ring clamping edge, which protrudes radially outwards into a clamping groove 20, which in turn transitions into a flattened ring edge 26.

Accordingly, the clamping membrane 8 is sealed with the aid of the aforementioned sealing or welding 15, 16 on the holder end 22, which protrudes flatly to the outside, and attached under a high load.

In the exemplary embodiment shown, the object 2 to be held has a holding slot 5, which can be plugged in a clamping fashion onto an allocated holding edge 24 on the inside of the lower part 4.

Instead of such a plug-in connection, other fixing options can of course also be used. It is preferably preferred if a fixing device 23 is present between the object to be maintained 2 and the inside of the sub-part 4, which can also be configured as a screw connection, terminal connection, wedge connection or bayonet rotating connection.

The lower part 4 comprises a sealing finger 25, which protrudes radially inside into the cover 3 and extends radially out into a ring groove 27, which in turn connects radially outwards to latching edge 28, on whose free end an inward-facing hook edge 29 is formed.

If the cover 3 is pushed onto the lower part 4, as shown in FIGS. 9 and 10, then the two sealing fingers 21 and 25 slide past each other and clamp the clamping membrane 8 between them and tension it into the clamping groove 20, which creates an additional tension on the clamping membrane 8 in the direction of the arrows 11.

Thus, two radially spaced sealing edges 31, 32 are simultaneously created, which ensure a reliable seal between the cover and the lower part 4 and form a double sterile barrier.

In a preferred exemplary embodiment, a locking between the cover 3 and the lower part 4 is provided in such a way that the ring edge 26 protruding horizontally to the outside engages with the assigned ring groove 27 on the bottom part 4 and the hook edge 29 snaps onto the ring edge 26 of the cover 3, resulting in a high-load latch connection.

FIG. 4 shows that, due to the pushing of the object 2 into the sealed interior 9 of the cover 3, a compression of the air contained therein occurs, whereby the clamping membrane 8 on the one hand is pretensioned in the direction of the arrow 11 and on the other hand forms a membrane bulge 8', which peripherally encompasses the object 2 to be held and ensures an additional position securing.

According to a preferred feature, the formation of the membrane bulge 8' is also a sign of the presence of the sealing effect of the two radially spaced sealing edges 31, 32. Even if such a medical sterile packaging is stored over a long period of time, it can be checked through visual inspection of the (preferably transparent) container as to whether the membrane bulge 8' is still present. If it is present, the tightness of container 1 is guaranteed. If it has disappeared, then a slackening of the clamping membrane 8 or even a leakage of the container 1 must be assumed. Thus, the specified container 1 is preferably suitable for long-term holding of highly sterile objects while maintaining its sealing effect due to the two spaced sealing wells 31, 32.

Figure 11:
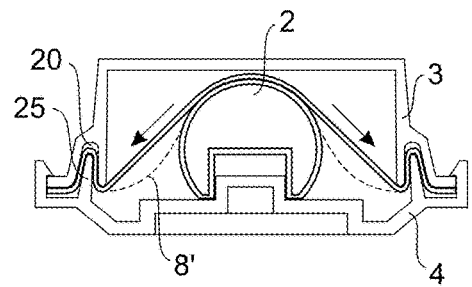
FIG. 11 shows the container according to FIGS. 8 to 10 in a first embodiment with a high clamping edge.

FIGS. 11 to 15 show various variations of the two spaced sealing edges 31, 32, wherein FIG. 11 shows that the height of the sealing finger 25 on the lower part is approximately 8 mm, and the sealing finger 25 engages almost completely into the clamping groove 20 on the cover. The maximum pretensioning of the clamping membrane 8 is thus carried out in the direction of the arrows 11 with the formation of a membrane bulge 8', as shown in FIG. 11.

Figure 12:
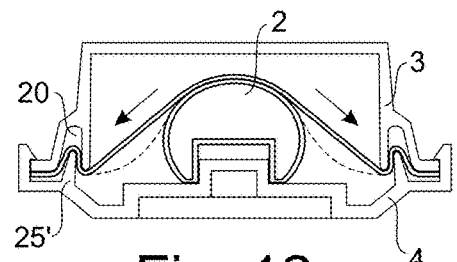
FIG. 12 shows a variant of FIG. 11 with an average clamping edge.

FIG. 12 shows that a lower sealing finger 25' can be used, which only partially engages in the clamping groove 20, but nevertheless the two radially spaced sealing edges 31, 32 are still present.

Figure 13:
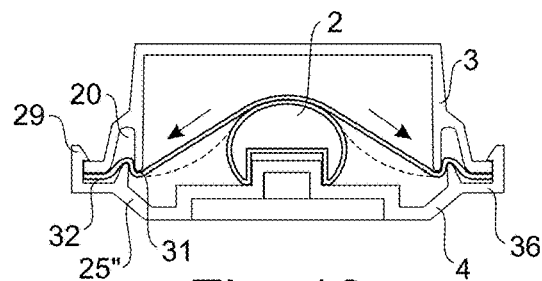
FIG. 13 shows a variant of FIG. 12 with a low clamping edge.

FIG. 13 shows an only 3 mm high sealing finger 25", which only negligibly engages in the clamping groove 20 of the cover 3 and ensures a lower pretensioning of the clamping membrane 8. Nevertheless, the sealing edges of 31 and 32 are still present.

Figure 14:
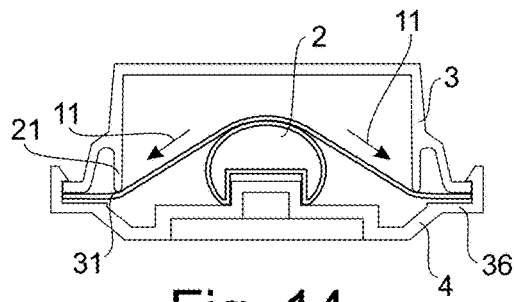
FIG. 14 shows a variant of FIG. 13 omitting one clamping edge, wherein a further clamping edge remains in place.

FIG. 14 shows that the sealing finger 25" can also be completely omitted, and only the cover-side sealing finger 31 is present, because only the one sealing edge 31 is present, while the other sealing edge 32 is omitted.

Figure 15:
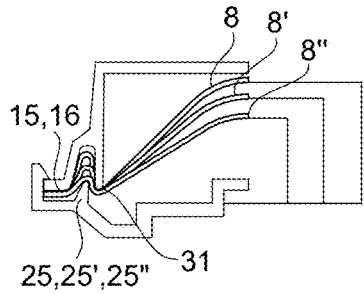
FIG. 15 shows a schematic view of the illustration of the various clamping edge heights according to FIGS. 11 to 13.

FIG. 15 shows the various exemplary embodiments according to FIGS. 11 to 13, summarized in a single figure, where it is discernible that despite different heights of the sealing fingers 25, 25', 25", the two sealing edges 31, 32 are maintained, however, the clamping membrane 8, 8', 8" has different heights and clamping effects.

Figure 16:
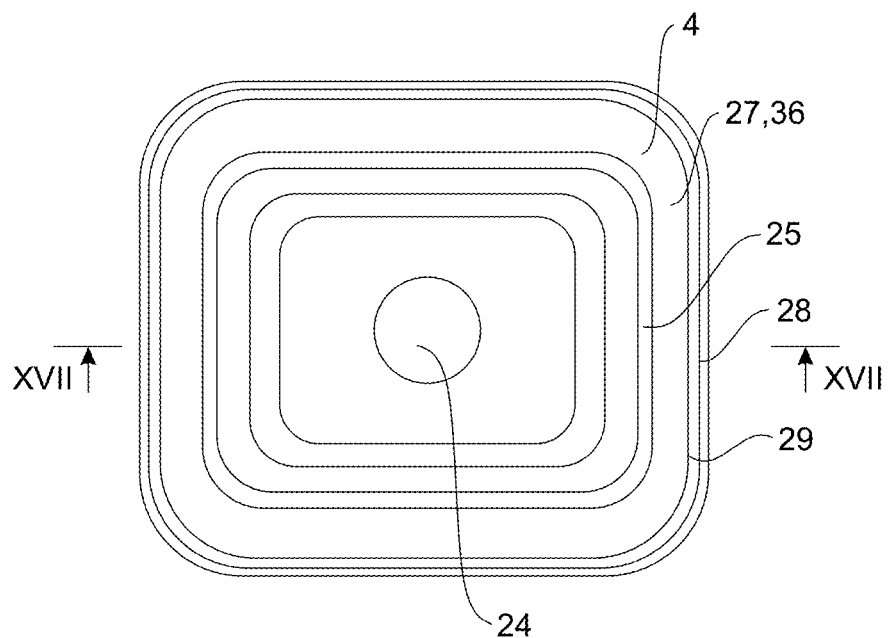
FIG. 16 shows a top view on the lower part.
Figure 17:
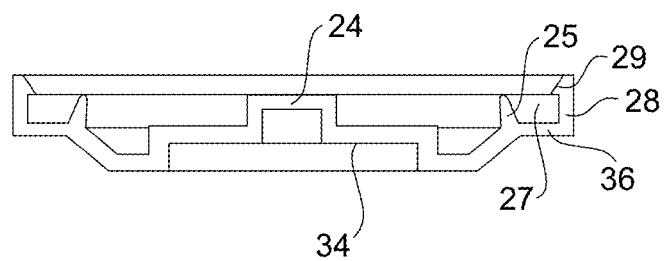
FIG. 17 shows across-section according to line XVII-XVII in FIG. 16.

FIGS. 16 and 17 show the internal view of the cover 4, where the same parts bear the same reference signs. It is discernible that the holding edge 24 is formed in a ring-shaped manner. However, it can take any other form, such as a triangular shape, a square shape, or the like.

It is further shown that the outside of the cover 4 has a recessed floor area 34, in whose area a label, instructions for use, or a booklet can be inserted.

Figure 18:
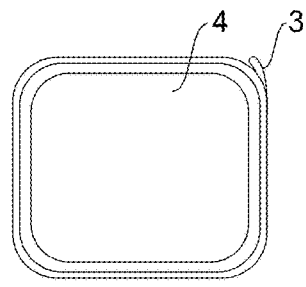
FIG. 18 shows a top view on a variant of the lower part with a pull tab.
Figure 19:
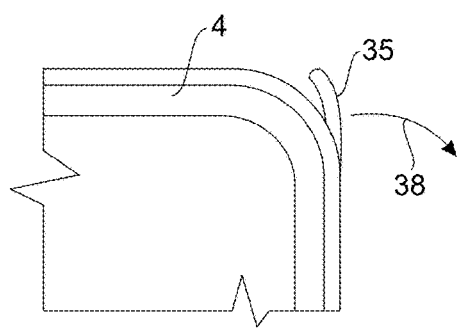
FIG. 19 shows the enlarged illustration according to FIG. 18.

FIGS. 18 and 19 show an embodiment modified from FIGS. 16 and 17, in which the latching connection is secured between the cover 3 and the lower part 4 by means of a pull tab 35, and the latching connection between the cover 3 and the lower part 4 can be detached upon pulling of the pull tab 35 in the direction of the arrow 38.

This is a tamper-proof seal, which is formed by the pull tab 35.

Figure 20:
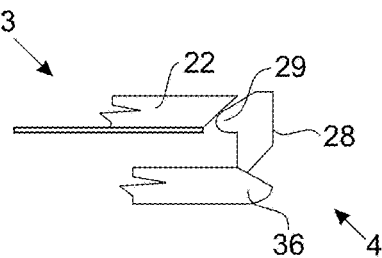
FIGS. 20 to 23 show the illustration of the latching of the cover and lower part, which can be separated from each other upon pulling of the pull tab.
Figure 21:
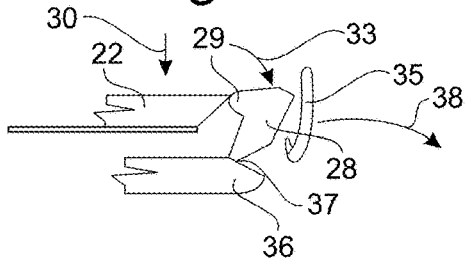
Figure 22:
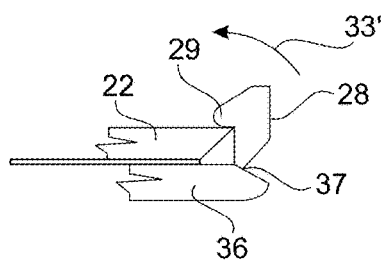
Figure 23:
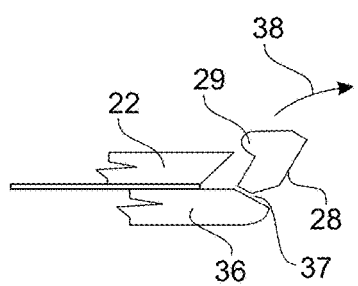

First, in FIGS. 20 to 22, the latching between the cover 3 and the lower part 4 is illustrated, where it is discernible that the holding edge 22 of the cover 3 has a rising slope, which interacts with the assigned latching edge 28 on the lower part and the hook edge 29 arranged there.

Accordingly, if the cover 3 is pushed down against the lower part 4 in the direction of the arrow 30, then the latching edge 28 moves outwardly, as shown in the direction of the arrow 33.

When producing a complete latching effect, it snaps back in the direction of the arrow 33' (see FIG. 22), whereby the completely sealed latching connection between the cover 3 and the lower part 4 is created.

If the pull tab 35 is now pulled up in the direction of the arrow 38, then the latching edge 28 is thus pulled out to the outside in the direction of the arrow 33 due to an existing target breaking ring groove 37 and detaches from the ring flange 36 of the lower part 4.

The latching connection between the cover 3 and the lower part 4 is thus lifted and also cannot be produced again, because the cover-side latching edge 28 has been separated.

FIGS. 24 to 27 show a further embodiment of a latching connection between the cover 3 and the lower part 4, wherein a number of clamping closures 39 are preferably present on the lower part 4, equally distributed on the perimeter, each of which is formed as an elastically bendable lobe, which is slightly bendable through assigned recesses 42. These are easily bendable and pivotable in the area of the film hinges 43 on the outer perimeter of the lower part 4.

FIG. 24 shows the open position of the clamping locks 39, while FIG. 25 shows the closed position and the latching position with the cover 3.

According to FIG. 26, the latching connection occurs in that the clamping lock 39 comprises a clamping edge 40 facing outwards, which comprises inward facing knobs 44, which can be latched into the assigned recesses 45 on the edge of the lower part 4.

A further securing of this locking connection—which can be closed in the direction of the arrow 41—occurs in that a recess 47 is present on the inside of the respective recess 42, which is latchable to an assigned knob 46 on the circumferential edge of the cover 3.

FIG. 27 shows the completely latched position, where the clamping edge 40 is latched by engagement of the knob 46 into the recess 47 and simultaneously the knob 44 is engaged with the lower part recess 45 in the lower area of the clamping lock 39.

It is self-evident that, in a kinematic inversion, the knobs 44 and 46 shown here can be replaced by recesses, and the recesses 45 and 47 shown here can be configured as knobs.

FIG. 27 also shows the radially spaced sealing edges 31 and 32, which are achieved by engagement [of] the lower part sealing finger 25 into the cover-side clamping groove 20.

Figure 28:
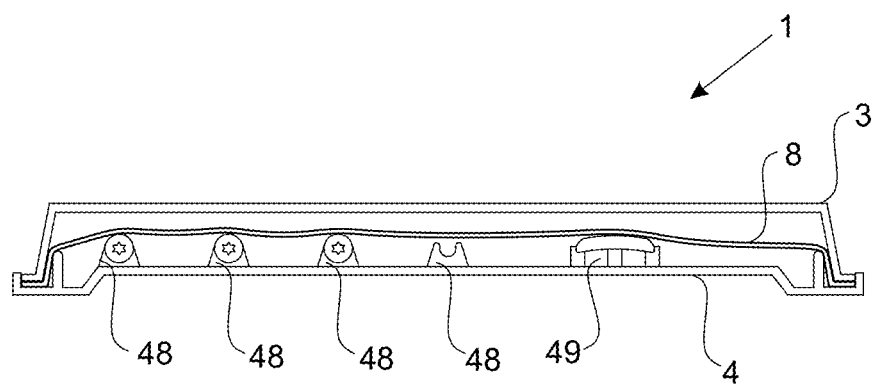
FIG. 28 shows a schematic cut through the cover and the lower part for holding several implant items.
Figure 29:
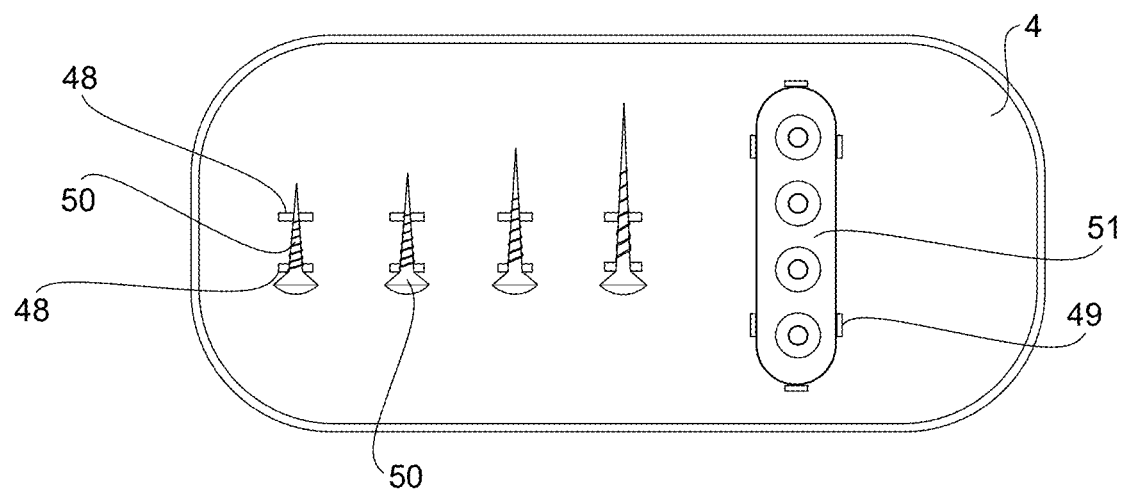
FIG. 29 shows the top view on the arrangement according to FIG. 28.

FIGS. 28 and 29 now show that in such a container 1, various objects can be held, wherein in the exemplary embodiment shown, a number of implant screws 50 are pinched in the clamping slots 48 and additionally an implant rail 51 is also provided, which is similarly held in a clamping slot 49.

The entire arrangement is covered by the cover 3 in the circumferentially sealed clamping membrane 8, wherein, even in such a complex fastening case, membrane bulges 8' are formed around the respective objects 50, 51 to be held, thereby allowing additional verification of the tightness of the entire container even in the case of long-term storage.

LEGEND OF THE DRAWINGS

| | |
|---|---|
| 1 | Container |
| 2 | Object |
| 3 | Cover |
| 4 | Lower part |
| 5 | Holding slot |
| 6 | Pivotal axis |
| 7 | Direction of the arrow |
| 8 | Clamping membrane |
| 8a, 8b, 8' | Membrane bulge |
| 9 | Interior (of 3) |
| 10 | Intermediate space |
| 11 | Direction of the arrow |
| 12 | Edge |
| 13 | Edge |
| 14 | Latching |
| 15 | Sealing edge |
| 16 | Sealing surface |
| 17 | Multiple containers |
| 18 | Target breaking point |
| 19 | Direction of the arrow |
| 20 | Clamping groove |
| 21 | Sealing finger (in 3) |
| 22 | Holding edge (of 3) |
| 23 | Fixing device |
| 24 | Holding edge |
| 25 | Sealing finger (in 4) |
| 26 | Ring edge |
| 27 | Annular groove |
| 28 | Latching edge |
| 29 | Hook edge |
| 30 | Direction of the arrow |
| 31 | Sealing edge (inside) |
| 32 | Sealing edge (outside) |
| 33 | Direction of the arrow |
| 34 | Floor surface (in 4) |
| 35 | Pull tab |
| 36 | Ring flange |
| 37 | Target break ring groove |
| 38 | Direction of the arrow |
| 39 | Clamping lock |
| 40 | Clamping edge |
| 41 | Direction of the arrow |
| 42 | Recess |
| 43 | Film hinge |
| 44 | Nub |
| 45 | Recess |
| 46 | Nub |
| 47 | Recess |

-continued

| | |
|---|---|
| 48 | Clamping slot |
| 49 | Clamping slot |
| 50 | Implant screw |
| 51 | Implant rail |
| 52 | Holding surface |

What is claimed is:

1. A container for medical objects, the container comprising:
at least one cover connectable to a lower part,
wherein the container comprises a clamping membrane circumferentially and peripherally attached to either of the at least one cover or the lower part, and a fixing device arranged in the other of the at least one cover or the lower part,
wherein the fixing device comprises a holding edge for holding a medical object thereon, wherein the fixing device comprises a plug-in device, a clamping device, or a screw-on device specifically configured for the object to be held,
wherein the clamping membrane is pushed into an interior of the container upon connecting the at least one cover and the lower part to close the container when a medical object is held on the fixing device,
wherein each of the at least one cover and the lower part comprise a circumferential, peripheral annular groove having a sealing finger,
wherein connecting the at least one cover to the lower part to close the container brings the annular grooves together such that the sealing fingers interact to form two circumferential sealing edges radially distanced from one another,
wherein the clamping membrane is attached in a sealing manner and, upon connection of the at least one cover and the lower part to close the container, is tensioned on all sides by the two circumferential sealing edges, and
wherein a peripheral edge of either of the at least one cover or the lower part comprises a clamping lock.

2. The container of claim 1, wherein the clamping membrane is attached to the at least one cover in the sealing manner to form an interior that is sealed against the atmosphere, wherein the interior is gas filled so that pushing the clamping membrane into the interior causes an over-pressure of the gas leading to a membrane bulge.

3. The container of claim 2, wherein the membrane bulge forms around a medical object held by the holding edge of the fixing device of the lower part when the medical object is contained within the closed container.

4. The container of claim 2, wherein at least one of the at least one cover and the lower part is at least partially transparent so that the membrane bulge can be visually inspected to verify tightness of a seal when a medical object is contained within the closed container.

5. The container of claim 1, wherein the clamping membrane is attached to the at least one cover in the sealing manner, and wherein the sealing fingers of the annular grooves on each of the at least one cover and the lower part interact to push the clamping membrane into the clamping groove to tension the clamping membrane on all sides.

6. The container of claim 1, wherein the clamping lock comprises a hook edge on the lower part that snaps over a holding edge of the at least one cover to form a latch connection when the lower part and the at least one cover are connected to close the container.

7. The container of claim 1, wherein one of the at least one cover or the lower part comprises the clamping lock, wherein the clamping lock is configured to engage a peripheral edge of the other of the at least one cover or the lower part to securely latch the closed container.

8. The container of claim 7, wherein the closed container is unlatched by means of a pull tab formed as a tamper-proof seal.

9. The container of claim 1, wherein the lower part comprises the clamping lock configured to close over a peripheral edge of the at least one cover to securely latch the closed container.

10. The container of claim 9, wherein the clamping lock comprises a recess that engages with a nub on the peripheral edge of the at least one cover.

11. The container of claim 9, wherein the clamping lock comprises a clamping edge facing outwards, wherein the clamping edge comprises inward facing knobs that are latchable into recesses on a circumferential edge of the lower part.

12. A container for medical objects, the container comprising:
  at least one cover having a clamping membrane circumferentially and peripherally attached thereon; and
  a lower part having a fixing device comprising a holding edge for holding a medical object thereon,
  wherein the fixing device comprises a plug-in device, a clamping device, or a screw-on device specifically configured for the medical object to be held,
  wherein the clamping membrane is attached to the at least one cover in a sealing manner to form an interior sealed against the atmosphere,
  wherein the interior is gas filled so that pushing the clamping membrane into the interior causes an overpressure of the gas leading to a membrane bulge, and
  wherein interlocking the at least one cover and the lower part to close the container leads to a circumferential, peripheral pretensioning of the clamping membrane on all sides and pushes the clamping membrane to the interior of the container when the fixing device has the medical object held thereon.

13. The container of claim 12, wherein the at least one cover comprises a circumferential, peripheral clamping groove and the lower part comprises a circumferential, peripheral annular groove, and wherein connecting the at least one cover to the lower part to close the container interlocks the clamping groove with the annular groove to pretension the clamping membrane.

14. The container of claim 13, wherein each of the clamping groove and the annular groove comprise a sealing finger that upon interlocking the clamping groove with the annular groove pushes the clamping membrane into the clamping groove to pretension the clamping membrane on all sides.

15. The container of claim 12, wherein the at least one cover comprises a circumferential, peripheral clamping groove having a sealing finger, such that upon connecting the at least one cover and the lower part to close the container, the sealing finger pretensions the clamping membrane on all sides.

16. The container of claim 12, wherein at least one of the at least one cover and the lower part is at least partially transparent so that the membrane bulge can be visually inspected to verify tightness of a seal when a medical object is contained within the closed container.

* * * * *